(12) United States Patent
Ierulli (10) Patent No.: US 11,344,444 B2
(45) Date of Patent: May 31, 2022

(54) NASAL DILATORS WITH IMPROVED BREATHABILITY

(71) Applicant: Joseph V. Ierulli, Bradenton, FL (US)

(72) Inventor: Joseph V. Ierulli, Bradenton, FL (US)

(73) Assignee: Corbett Lair Inc., Bradenton, FL (US)

( * ) Notice: Subject to any disclaimer, the term of this patent is extended or adjusted under 35 U.S.C. 154(b) by 391 days.

(21) Appl. No.: 16/377,198

(22) Filed: Apr. 6, 2019

(65) Prior Publication Data

US 2020/0315835 A1 Oct. 8, 2020

(51) Int. Cl.
*A61F 5/08* (2006.01)

(52) U.S. Cl.
CPC ...................... *A61F 5/08* (2013.01)

(58) Field of Classification Search
CPC .. A61F 5/08; A61F 2210/0076; A61F 13/126; A61M 29/00; A61D 7/04
USPC .................................... 606/204.45
See application file for complete search history.

(56) References Cited

U.S. PATENT DOCUMENTS

| | | |
|---|---|---|
| 5,476,091 A | 12/1995 | Johnson |
| 5,479,944 A | 1/1996 | Petruson |
| 5,533,499 A | 7/1996 | Johnson |
| 5,533,503 A | 7/1996 | Doubek et al. |
| 5,546,929 A | 8/1996 | Muchin |
| 5,549,103 A | 8/1996 | Johnson |
| RE35,408 E | 12/1996 | Petruson |
| 5,611,333 A | 3/1997 | Johnson |
| 5,653,224 A | 8/1997 | Johnson |
| 5,706,800 A | 1/1998 | Cronk et al. |
| 5,718,224 A | 2/1998 | Muchin |
| 5,769,089 A | 6/1998 | Hand et al. |
| 5,890,486 A | 4/1999 | Mitra et al. |
| 5,931,854 A | 8/1999 | Dillon |
| 5,957,126 A | 9/1999 | Neeser |
| 6,006,746 A | 12/1999 | Karell |
| 6,029,658 A | 2/2000 | De Voss |
| 6,033,422 A * | 3/2000 | Blach .................. A61D 7/04 128/200.24 |
| 6,058,931 A | 5/2000 | Muchin |
| 6,065,470 A | 5/2000 | Van Cromvoirt et al. |
| 6,098,616 A | 8/2000 | Lundy et al. |
| 6,196,228 B1 | 3/2001 | Kreitzer et al. |
| 6,244,265 B1 | 6/2001 | Cronk et al. |
| 6,276,360 B1 | 8/2001 | Cronk et al. |

(Continued)

FOREIGN PATENT DOCUMENTS

| | | |
|---|---|---|
| EP | 355175 A1 | 7/1998 |
| ES | 289561 | 10/1985 |

OTHER PUBLICATIONS

Office Action dated Apr. 21, 2021 for U.S. Appl. No. 16/377,196.

*Primary Examiner* — Kathleen S Holwerda
(74) *Attorney, Agent, or Firm* — GrayRobinson, P.A.

(57) ABSTRACT

Nasal dilators with improved comfort are formed as a laminate of layers: a resilient layer including a plurality of resilient members; and an engagement layer including one or both of a base layer and a cover layer. A portion of the dilator occupied by all of the resilient members plus the gap(s) between the resilient members has a total area, and the proportion of that area that is occupied or covered by the resilient members does not exceed 57%. Preferably, the proportion is lower than about 50%, and it may be as low as 30% in some embodiments.

14 Claims, 6 Drawing Sheets

(56) References Cited

U.S. PATENT DOCUMENTS

| | | | |
|---|---|---|---|
| 6,318,362 B1 | 11/2001 | Johnson |
| 6,357,436 B1 | 3/2002 | Kreitzer et al. |
| 6,375,667 B1 | 4/2002 | Ruch |
| 6,453,901 B1 | 9/2002 | Ierulli |
| 6,470,883 B1 | 10/2002 | Beaudry |
| 6,550,474 B1 | 4/2003 | Anderson et al. |
| 6,694,970 B2 | 2/2004 | Spinelli et al. |
| 6,769,428 B2 | 8/2004 | Cronk et al. |
| 6,769,429 B1 | 8/2004 | Benetti |
| 7,067,710 B1 | 6/2006 | Beaudry |
| 7,114,495 B2 | 10/2006 | Lockwood, Jr. |
| D639,762 S | 6/2011 | Brogden et al. |
| D644,325 S | 8/2011 | Brunner et al. |
| D644,324 S | 10/2011 | Brunner et al. |
| 8,047,201 B2 | 11/2011 | Guyuron et al. |
| 8,062,329 B2 | 11/2011 | Ierulli |
| D651,710 S | 1/2012 | Brogden et al. |
| 8,115,049 B2 | 2/2012 | Beaudry |
| D659,245 S | 5/2012 | Ierulli |
| 8,188,330 B2 | 5/2012 | Beaudry |
| D662,203 S | 6/2012 | Smith |
| D667,543 S | 9/2012 | Ierulli |
| D671,643 S | 11/2012 | Ierulli |
| D672,461 S | 12/2012 | Brogden et al. |
| D672,872 S | 12/2012 | Brunner et al. |
| D673,270 S | 12/2012 | Brunner et al. |
| 8,342,173 B2 | 1/2013 | Lockwood, Jr. |
| 8,444,670 B2 | 5/2013 | Ierulli |
| 8,584,671 B2 | 11/2013 | Ierulli |
| 8,616,198 B2 | 12/2013 | Guyuron et al. |
| 8,617,199 B2 | 12/2013 | Eull et al. |
| 8,641,852 B2 | 2/2014 | Ierulli |
| D707,814 S | 6/2014 | Ierulli |
| D707,815 S | 6/2014 | Ierulli |
| 8,834,511 B2 | 9/2014 | Holmes et al. |
| 8,834,512 B1 | 9/2014 | Brown et al. |
| 8,834,514 B2 | 9/2014 | Smith |
| 8,858,587 B2 | 10/2014 | Ierulli |
| D722,161 S | 2/2015 | Reyers |
| D722,162 S | 2/2015 | Reyers |
| D725,772 S | 3/2015 | Ierulli |
| D725,773 S | 3/2015 | Ierulli |
| 9,095,422 B2 | 8/2015 | Gray |
| D738,496 S | 9/2015 | Peck |
| D739,015 S | 9/2015 | Martin |
| 9,119,620 B2 | 9/2015 | Peterson et al. |
| D741,997 S | 10/2015 | Terulli |
| D741,998 S | 10/2015 | Martin |
| D743,544 S | 11/2015 | Ierulli |
| D743,545 S | 11/2015 | Ierulli |
| D743,565 S | 11/2015 | Engel et al. |
| D745,147 S | 12/2015 | Ierulli |
| 9,204,988 B1 | 12/2015 | Fischell |
| D746,982 S | 1/2016 | Ierulli |
| D747,478 S | 1/2016 | Brunner et al. |
| D753,294 S | 4/2016 | Guyuron et al. |
| D755,376 S | 5/2016 | Ierulli |
| D758,575 S | 6/2016 | Ierulli |
| D758,576 S | 6/2016 | Ierulli et al. |
| D759,240 S | 6/2016 | Ierulli |
| D759,241 S | 6/2016 | Ierulli |
| D759,242 S | 6/2016 | Ierulli |
| 9,364,367 B2 | 6/2016 | Ierulli |
| 9,364,368 B2 | 6/2016 | Ierulli |
| 9,381,332 B2 | 7/2016 | Judd |
| D764,055 S | 8/2016 | Ierulli et al. |
| D764,662 S | 8/2016 | Ierulli et al. |
| 9,414,957 B1 | 8/2016 | Fischell |
| 9,427,945 B2 | 8/2016 | Gray et al. |
| D779,666 S | 2/2017 | Ierulli et al. |
| D779,667 S | 2/2017 | Ierulli et al. |
| 9,566,183 B1 | 2/2017 | Fischell |
| D788,298 S | 5/2017 | Guyuron |
| 9,642,995 B2 | 5/2017 | Fenton et al. |
| D789,531 S | 6/2017 | Ierulli |
| D790,058 S | 6/2017 | Ierulli et al. |
| D790,695 S | 6/2017 | Ierulli |
| D791,312 S | 7/2017 | Peck |
| D791,314 S | 7/2017 | Ierulli |
| 9,730,827 B2 | 8/2017 | Ierulli |
| 9,730,828 B2 | 8/2017 | Ierulli |
| 9,775,738 B2 | 10/2017 | Andre |
| 9,844,456 B2 | 12/2017 | Ierulli |
| 9,901,479 B2 | 2/2018 | Holmes |
| 9,901,480 B2 | 2/2018 | Ierulli |
| 9,901,481 B2 | 2/2018 | Ierulli |
| D812,749 S | 3/2018 | Ierulli |
| D813,387 S | 3/2018 | Ierulli et al. |
| D814,029 S | 3/2018 | Ierulli |
| 10,010,442 B2 | 7/2018 | Ierulli et al. |
| 1,149,781 A1 | 12/2018 | Ierulli |
| 10,328,625 B2 | 6/2019 | Gray et al. |
| 2008/0058858 A1 | 3/2008 | Smith |
| 2008/0097517 A1 | 4/2008 | Holmes et al. |
| 2008/0177253 A1 | 7/2008 | Boehringer et al. |
| 2008/0257341 A1* | 10/2008 | Ierulli .................. A61F 5/08 128/200.24 |
| 2009/0125052 A1 | 5/2009 | Pinna et al. |
| 2009/0234383 A1 | 9/2009 | Ierulli |
| 2010/0210988 A1 | 8/2010 | Dallison |
| 2010/0298861 A1 | 11/2010 | Fenton |
| 2011/0000483 A1 | 1/2011 | Matthias et al. |
| 2011/0054517 A1 | 3/2011 | Holmes et al. |
| 2011/0166594 A1* | 7/2011 | Eull .................... A61F 5/08 606/201 |
| 2011/0224717 A1 | 9/2011 | Lockwood |
| 2012/0004683 A1 | 1/2012 | Gray |
| 2012/0022582 A1 | 1/2012 | Guyuron |
| 2012/0067345 A1 | 3/2012 | Shilon |
| 2012/0172923 A1 | 7/2012 | Fenton |
| 2012/0209313 A1 | 8/2012 | Ierulli |
| 2012/0232455 A1 | 9/2012 | Beaudry |
| 2013/0104882 A1 | 5/2013 | Ierulli |
| 2013/0118488 A1 | 5/2013 | Ledogar |
| 2014/0194922 A1 | 7/2014 | Ierulli |
| 2014/0148844 A1 | 10/2014 | Andre |
| 2014/0296904 A1 | 10/2014 | Andre |
| 2014/0350596 A1 | 11/2014 | Smith |
| 2015/0005812 A1 | 1/2015 | Holmes |
| 2015/0012035 A1 | 1/2015 | Ierulli |
| 2015/0051636 A1 | 2/2015 | Lockwood |
| 2015/0090398 A1 | 4/2015 | Ierulli |
| 2015/0090399 A1 | 4/2015 | Ierulli |
| 2015/0094757 A1 | 4/2015 | Ierulli |
| 2015/0094758 A1 | 4/2015 | Ierulli |
| 2015/0216709 A1 | 8/2015 | Peck |
| 2015/0230966 A1 | 8/2015 | Ierulli |
| 2015/0250637 A1 | 9/2015 | Ierulli |
| 2015/0290021 A1 | 10/2015 | Gray |
| 2015/0359654 A1 | 12/2015 | Bentivegna et al. |
| 2016/0008161 A1 | 1/2016 | Ierulli et al. |
| 2016/0278967 A1 | 9/2016 | Ierulli |
| 2016/0278968 A1 | 9/2016 | Ierulli |
| 2016/0339619 A1 | 11/2016 | Gray et al. |
| 2017/0112653 A9 | 4/2017 | Ierulli |
| 2017/0143531 A9 | 5/2017 | Ierulli |
| 2017/0151084 A9 | 6/2017 | Ierulli |
| 2018/0021163 A9 | 1/2018 | Ierulli |
| 2018/0028346 A1 | 2/2018 | Ierulli |
| 2018/0071131 A1 | 3/2018 | Ierulli |
| 2019/0167464 A1 | 6/2019 | Lovato |

\* cited by examiner

Prior Art ← — — — — — — — → Present Invention

NASAL DILATORS WITH IMPROVED BREATHABILITY

CONTINUITY AND CLAIM OF PRIORITY

This is an original U.S. patent application.

FIELD

The invention relates to nasal dilators. More specifically, the invention relates to nasal-dilator configurations that provide improved wearing comfort.

BACKGROUND

Dilators to improve breathing by expanding a person's nasal passages have been investigated and developed for many decades. One of the earliest external nasal dilator devices is described in U.S. Pat. No. 1,292,083 to Sawyer, and a simple forerunner of contemporary external nasal dilators was described in Spanish utility model ES_289-561 in 1985.

Figure 3A:
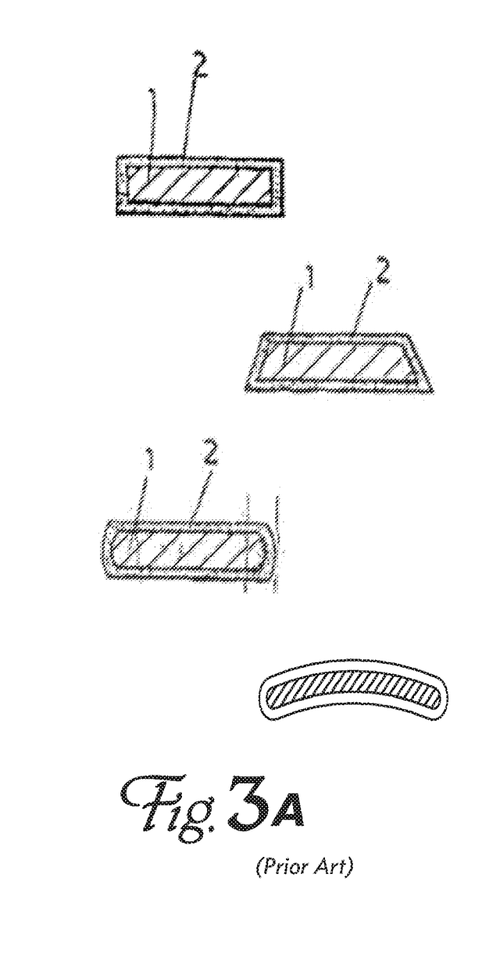
FIGS. 3A-3C show examples of prior-art dilators of the three major categories.
Figure 3B:
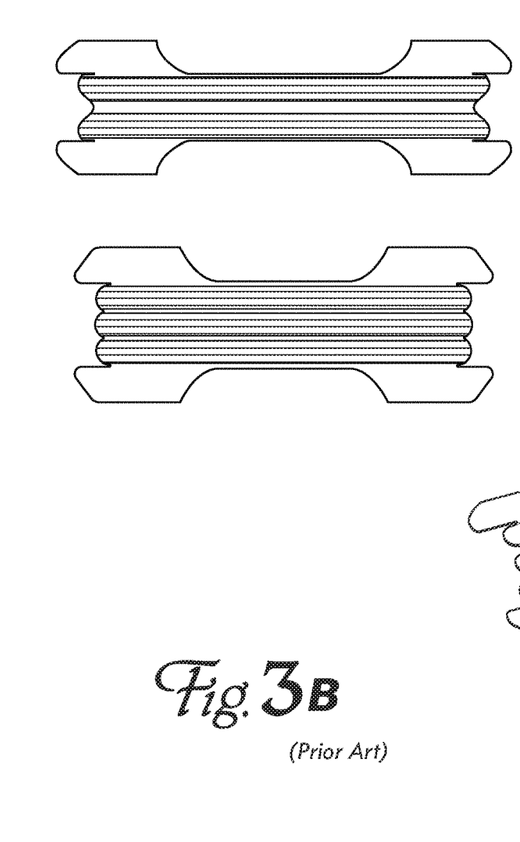
Figure 3C:
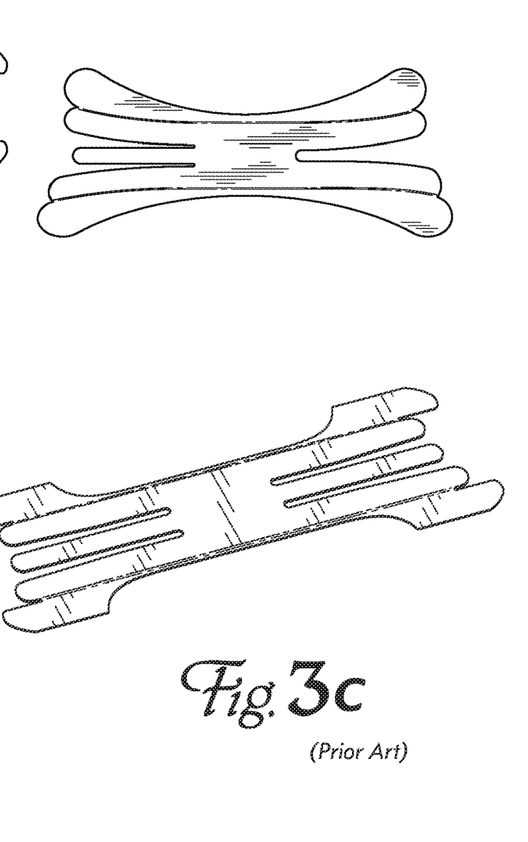

With the development of modern materials (including nonwoven fabrics, breathable films, and sturdy, lightweight resilient plastic sheet materials), most recent dilators have adopted one of three basic forms, shown in FIGS. 3A-C. The simplest is a "hot dog" shape (FIG. 3A): a single resilient band (which may be straight or curved) is "island-placed" within the periphery of an adhesive material Slightly more complex is the "dog bone" shape (FIG. 3B), which includes enlarged end regions comprising corner tabs, or wings, to improve adherence, and so that the resilient members may extend fully from end to end. Dog-bone dilators typically have multiple parallel resilient members, and these are often constrained along their lengths, or at least at their ends, so as to be securely integrated into a truss-like configuration. Finally, "butterfly" dilators (FIG. 3c) have multiple separate spring fingers extending outward from a common center, intending to provide dilation at discrete points about the nose. Butterfly dilators may be distinguished from dog-bone dilators in part by the fact that the lateral ends of the resilient member(s) are not constrained relative to each other; their four (or more) resilient branches are relatively free to move independently.

Note that some prior-art dilators blur the boundaries between "hot dog," "dog bone" and "butterfly." For example, U.S. Pat. No. 5,533,499 to Johnson discloses a dilator whose overall shape is that of a dog bone, but whose resilient members terminate short of the dilator ends, so they are island-placed.

All contemporary dilators must address several common challenges: first, they must adhere securely enough to avoid peeling off inadvertently, yet not adhere so aggressively that the user's skin is damaged when they are removed intentionally. Second, they must be comfortable for long-term (often overnight) wear. And finally, they must provide a consistent, reliable spring force to stabilize the skin and tissue over the user's nasal valve, and thereby to help open the user's nasal passages for improved respiration.

One occurrence that adversely impacts user comfort is the accumulation of moisture under the dilator—the skin to which the dilator is adhered may transpire or sweat, and the combination of perspiration and adhesive may cause itching. In some embodiments, adhesive-free areas or even absorbent pads are used to reduce the area where itching may occur. Other designs use special materials with higher moisture vapor transmission rates (MVTR). However, these materials are often more expensive than traditional materials, or are harder to work with.

Alternative approaches to reducing moisture-trapping surface area in a nasal dilator may be of substantial value in this area of technology.

SUMMARY

Embodiments of the invention are dog-bone style nasal dilators whose resilient members are positioned differently from the prior art, so that the breathable surface area of the dilator within the resilient structure's boundaries is substantially increased.

DETAILED DESCRIPTION

Figure 1:
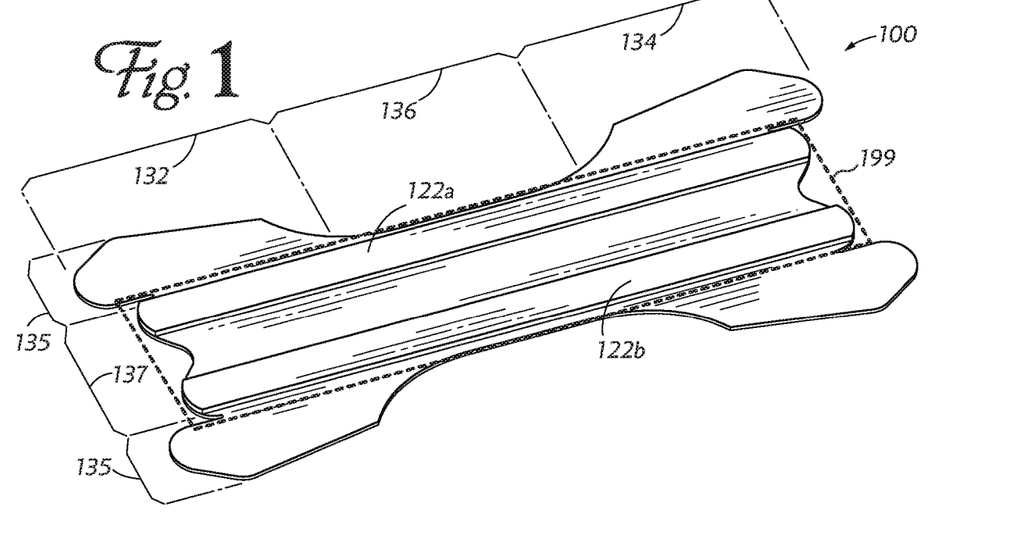
FIG. 1 shows a representative embodiment of the invention.

An embodiment of the invention is a dog-bone style nasal dilator, generally similar to the device 100 depicted in FIG. 1. Various regions of the dilator are identified in this figure, and the same terms will be used to refer to corresponding regions in both inventive and prior-art dilators.

Dilator 100 is an oblong structure which may be divided into three regions along its length: lateral end regions 132, 134 are interconnected by a narrower "waist" region 136. Similarly, across its width, the dilator may be divided into two outer portions 135 flanking a central band 137. The central band 137 includes two resilient members 122a, 122b, which extend fully from end to end of the dilator. (End-to-end resilient members allow the dilator to be manufactured more accurately and efficiently, compared to island-placed resilient members.) In use, the narrow waist region 136 is placed across the bridge of the nose, and the lateral end regions 132, 134 are pressed down and adhered against the sides of the nose and the cheeks. The resilient members are thus flexed over the bridge of the nose, and in attempting to spring back to their unflexed configuration, they lift and stabilize the skin to which they are adhered, thus opening and dilating the user's nasal passages. The outer portions 135 include corner tabs (sometimes called "tab extensions" or "wings") that aid in maintaining the lateral end regions 132 and 134 secured to the skin of the nose. The distinguishing characteristics of an embodiment lie mostly within the central band 137, which may be viewed as a "resilient structure bounding box" 199, outlined in heavy dashed lines.

Figure 2:
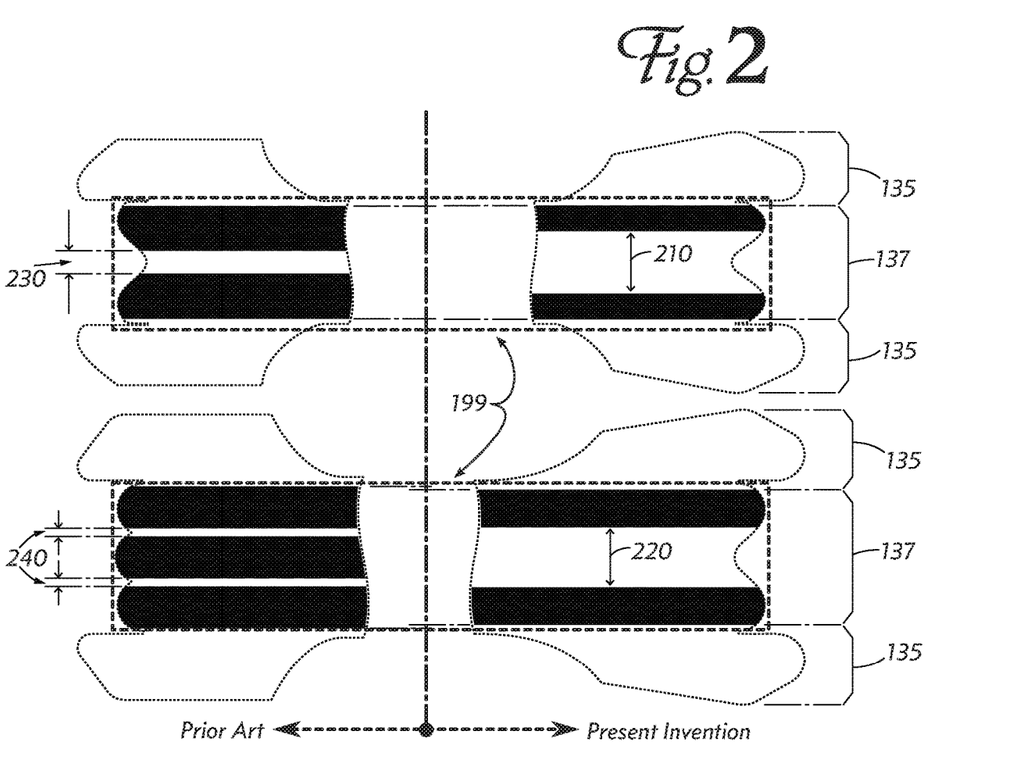
FIG. 2 highlights important differences between embodiments and prior-art dog-bone dilators.

FIG. 2 compares prior-art dogbone-style two- and three-band nasal dilators with nearly identically-sized two-band dilators according to embodiments of the invention. In this Figure, the resilient members are shown as solid black bars to highlight the substantial portion of the resilient structure bounding box 199 covered by prior-art resilient members, as compared to the significantly reduced proportion covered by the resilient members in embodiments of the invention. In the prior-art dilators, the resilient members are wider than those of the embodiment, and they are also positioned much closer together (compare 210, 220 with 230, 240). The result is that the ratio of the total area of the resilient structure bounding box 199 to the area of the bounding box covered by resilient-member material is much higher in the prior art. Prior-art structures may be as much as 90% covered, whereas an embodiment is 54% or less.

The difference in surface area coverage is important because the material used for all nasal dilator resilient members is typically a nonpermeable or low-permeability plastic such as polyethyl tetraphthalate ("PET" or biaxially-oriented polyethyl tetraphthalate, "boPET"). The other portions of the resilient member bounding box may be covered by a permeable material such as a woven or nonwoven fabric or a breathable plastic film (or, in some embodiments described below, by nothing at all—i.e., by an opening that exposes the skin directly to the atmosphere). By reducing the amount of skin covered by the resilient-member material, an embodiment improves skin breathability and reduces moisture vapor accumulation, and thus improves device comfort.

Figure 4A:
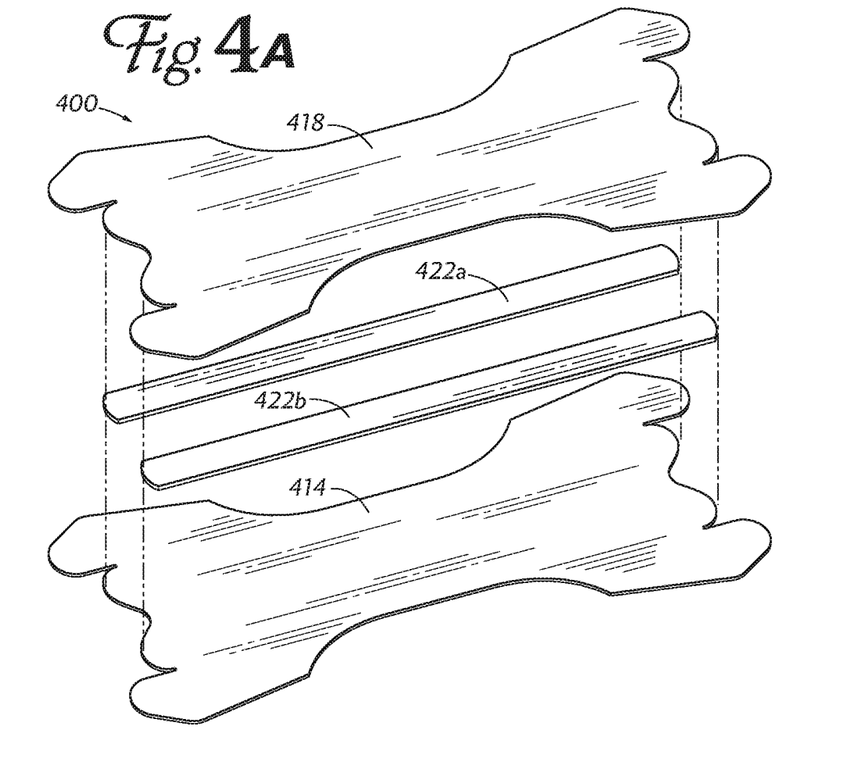
FIGS. 4A-4D show alternative material stacking orders in a laminated dilator according to an embodiment.
Figure 4B:
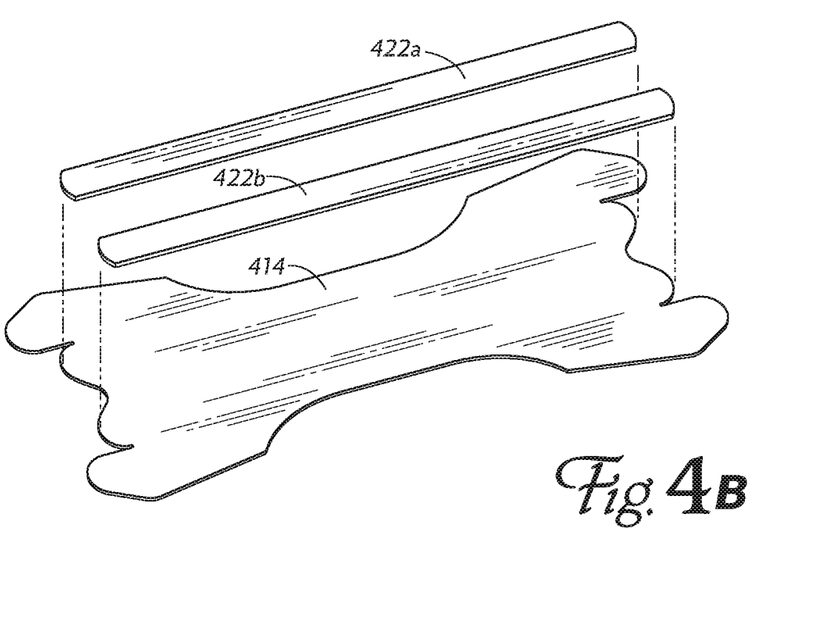
Figure 4C:
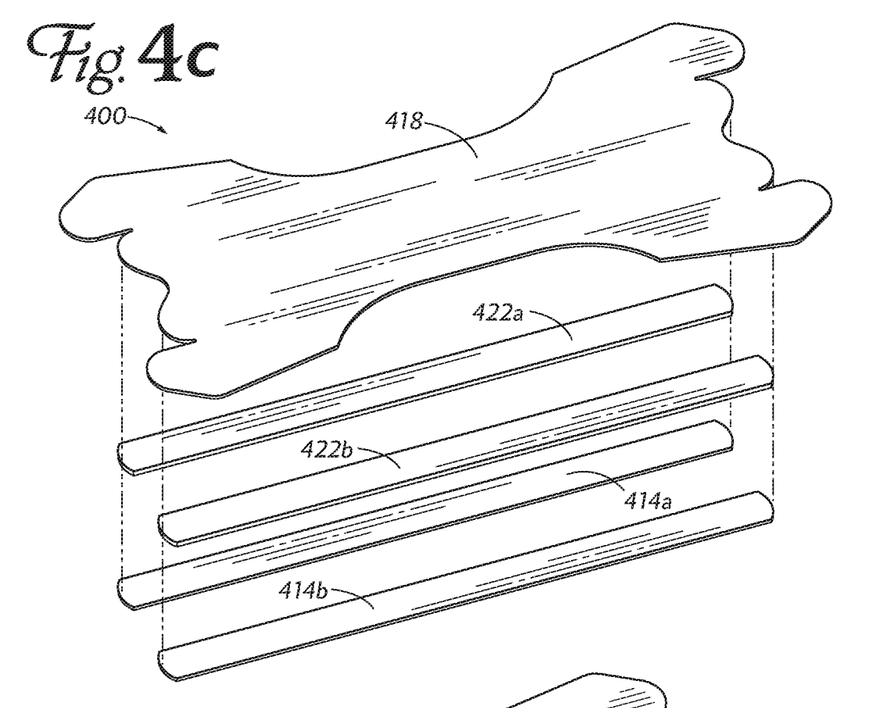
Figure 4D:
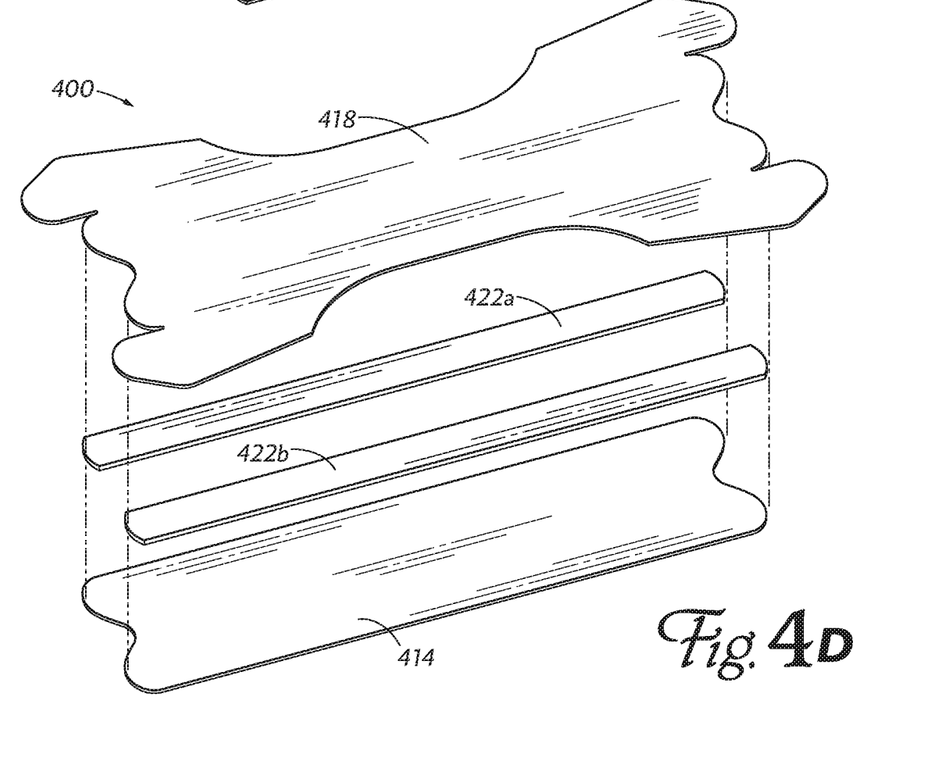

FIGS. 4A-4D show several different stacking orders for the materials that are laminated into a dilator according to an embodiment. Embodiments include a layer containing the resilient members (a "resilient layer"), and: 1) a cover layer over the resilient members; 2) a base layer under the resilient members; or 3) both a cover layer and a base layer. The cover and/or base layers define the outer peripheral boundary of the dilator, and are referred to generally as the "engagement layer." Those layers may be the same shape (i.e., the shape of the dilator outline), as shown in FIG. 4A, 414 and 418 are the same shape; or a layer may be the same shape as the resilient members (FIGS. 4c, 414a and 414b are the same shape as 422a and 422b, respectively); or the base layer may approximate the resilient-structure bounding box (FIG. 4D, base layer 414 covers just the bounding box 199); or the cover layer may be omitted entirely (FIG. 4B only includes base layer 414, which defines the dilator periphery). The various layer shapes and stacking configurations have ramifications in material use and ease of manufacture, as well as a modest effect on the performance of the dilator, but the exact choice of layers, layer shapes and stacking configuration are within the sound engineering judgment of one of ordinary skill, who can construct an embodiment by ensuring that the proportion of the resilient structure bounding box covered by resilient member material is less than a predetermined critical value.

Figure 5:
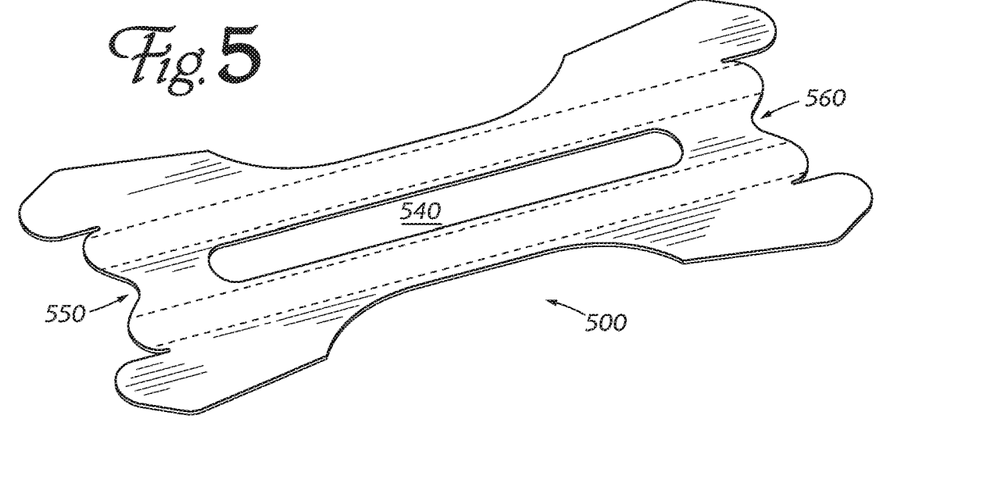
FIG. 5 shows another embodiment of the invention.

FIG. 5 shows another embodiment of the invention 500, where a central opening 540 has been made through the base and/or cover layers (through the engagement layer), between the resilient members, and not extending all the way to the lateral ends of the dilator, so that the resilient members are still constrained, effectively connected to each other at their lateral ends via the engagement layer (550, 560). Opening 540 has a higher moisture-vapor transmission rate ("MVTR") than even the permeable base and/or cover layer, so this dilator may be even more comfortable than a basic embodiment such as that shown in FIG. 1.

Figure 6:
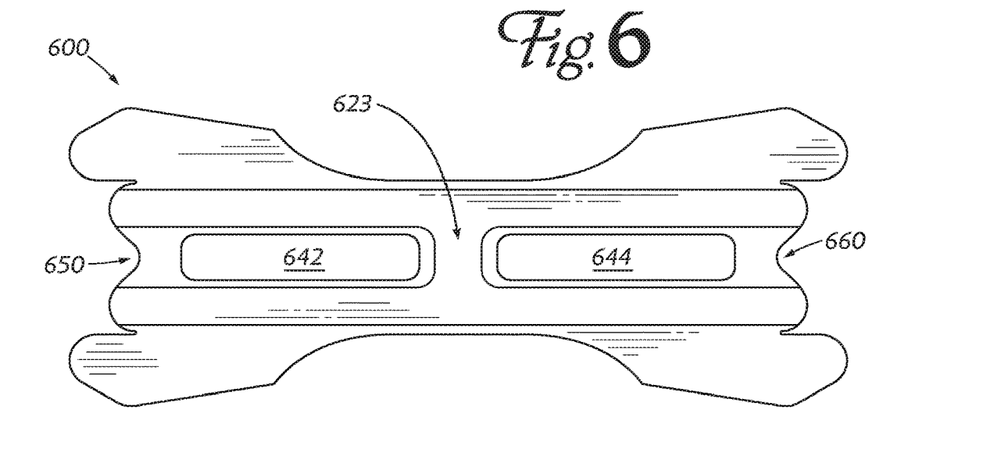
FIG. 6 shows another embodiment of the invention.

FIG. 6 shows another embodiment of the invention 600. Here, the resilient member bands are connected by a bridge in the center of the dilator (623), so they form an "H" shape, rather than two separate, parallel bands. Two openings 642, 644 expose skin on the sides of the user's nose and permit moisture to evaporate easily from the skin. This embodiment is different from the "butterfly" dilators because the ends of the resilient members—the tops and bottoms of the H shape—are still constrained: they are connected together by the base and/or cover layer (650, 660), whereas a butterfly dilator has resilient-member ends that can move independently.

Figure 7:
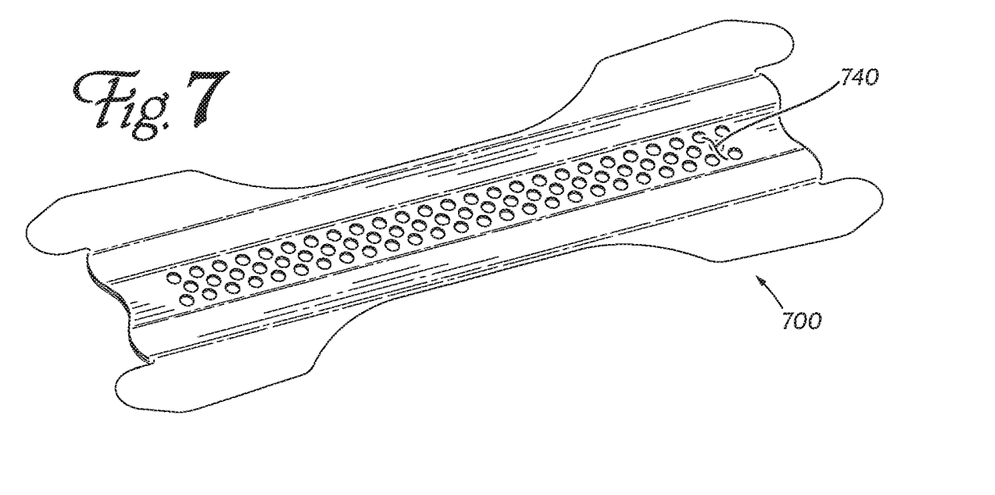
FIG. 7 shows another embodiment of the invention.

FIG. 7 shows another embodiment of the invention 700. This embodiment is similar to FIG. 1, 100 and FIG. 5, 500, but instead of a single large opening 540, the engagement layer between the resilient members and within the resilient structure bounding box is pierced by a plurality of openings 740. Thus, the high-MVTR area that is all consolidated into a single opening 540 in the embodiment of FIG. 5, is spread out somewhat in the embodiment of FIG. 7.

The principal distinguishing characteristic of an embodiment is the proportion of the resilient-member surface area that is covered by low-permeability or impermeable resilient members, compared to the total surface area of bounding box 199/central band 137. An embodiment reduces that proportion (with a corresponding increase in the higher-permeability area of non-resilient-member engagement layer surface area), by making the resilient members slightly narrower, and by separating the resilient members by a greater distance, while maintaining substantially the same central band width and spring force resiliency as the prior art. Some embodiments increase the effective MVTR of the bounding box area by piercing or removing some of the engagement layer within that area.

Note that the nasal dilator embodiments depicted in the foregoing figures are proportioned substantially accurately, although some material thicknesses are slightly exaggerated in some views for clarity. In particular, plan-view widths, lengths, and therefore surface areas, are proportioned so that they can be directly compared by visual inspection. Numerically, an embodiment is distinguished by a resilient structure bounding box where no more than 57.5% of the total area is occupied by low-permeability or impermeable resilient members. In other words, considering the length and width of the resilient members and the gap(s) separating them, the area covered by the resilient members is 57.5% or less. The thickness of the resilient members can be adjusted to increase resiliency as necessary to attain the target resilient or spring force, measured as detailed below, of between about 15 grams and about 45 grams.

In a preferred embodiment, the area of the resilient structure bounding box covered by low-permeability or impermeable resilient members is about 47%—less than half. An embodiment may comprise even narrower (though thicker) resilient members. The practical lower limit is about 40-43%—beyond that limit, the resilient members become unreasonably thick, complicating manufacturing procedures.

Figure 8A:
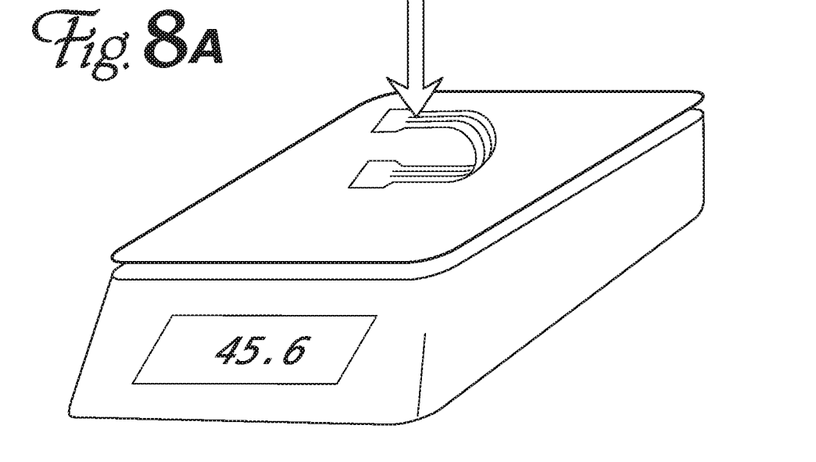
FIGS. 8A-8C show a protocol for measuring the resilient or spring force of a nasal dilator.
Figure 8B:
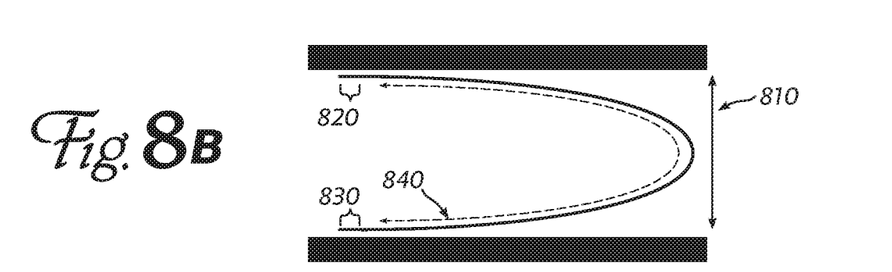
Figure 8C:
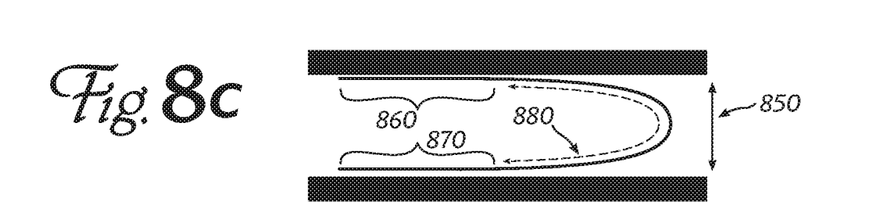

FIGS. 8A through 8C illustrate a protocol for measuring and comparing spring force resiliency between nasal dilators of the present invention and the prior art. As seen in FIG. 8A, a first end of the nasal dilator is forced toward its opposite end in a "U" shape, with one end placed flat against the surface of a scale. Only the very ends of the resilient members (820, 830) are forced to the parallel position between the scale surface and the pressing force (FIG. 8B, distance 810), so that the resiliency of almost the full length of the resilient structure, 840, can be measured. This arrangement yields the most accurate and repeatable readings of maximum spring force resiliency, and ensures a fair comparison between different nasal dilator devices. (It may be apparent to one of ordinary skill that if more pressure is applied to the resilient member, FIG. 8c, distance 850, then longer portions of the resilient member structure, 860 & 870, are forced parallel. This shortens the length of the measured portion of the resilient member, shown at 880, and gives an incorrect, high reading for the spring force.) This protocol is also believed to be a reasonable proxy for maximum in situ spring force resiliency, in that human noses are not typically narrower than the degree of dilator flexure caused by this measurement method.

The applications of the present invention have been described largely by reference to specific examples. Variations from the specific examples are understood to be captured according to the following claims.

I claim:

1. A nasal dilator formed as a laminate comprising an engagement layer and a resilient layer, the laminate having a plan-view periphery defined by the engagement layer, wherein:
    the resilient layer comprises two adjacent, parallel resilient bands extending fully from end to end of the nasal dilator, each band having a length, width and thickness,
    a width of a gap between the two adjacent, parallel resilient bands exceeds a width of either of the two adjacent, parallel resilient bands, and
    a spring force exerted by the two adjacent, parallel resilient bands flexed in a U shape so that their ends are roughly parallel is between 15 and 45 grams.

2. The nasal dilator of claim 1 wherein the gap between the two parallel resilient bands is constrained at at least both lateral ends of the two parallel resilient bands.

3. The nasal dilator of claim 2 wherein the gap between the two parallel resilient bands is constrained along substantially all of a length of the gap.

4. The nasal dilator of claim 1 wherein the resilient layer consists of the two parallel resilient bands.

5. The nasal dilator of claim 1 wherein the gap is spanned by a portion of the engagement layer, and wherein the portion of the engagement layer is fully pierced by at least one opening.

6. The nasal dilator of claim 5 wherein the at least one opening is two openings.

7. The nasal dilator of claim 5 wherein the at least one opening is an array of openings.

8. The nasal dilator of claim 1, wherein the two parallel resilient bands are integrated into the engagement layer by being constrained at both lateral ends thereof, respectively, by the engagement layer.

9. A nasal dilator formed as a laminate of a plurality of layers, including a resilient layer and at least one of a base layer and a cover layer, the nasal dilator characterized in that:
    the resilient layer occupies a roughly rectangular resilient layer bounding box;
    the resilient layer comprises a first resilient member extending along one long side of the resilient layer bounding box;
    the resilient layer comprises a second resilient member extending along another long side of the resilient layer bounding box;
    the first resilient member and the second resilient member are separated by a resilient member gap; and
    an area of the resilient layer bounding box covered by the first resilient member and the second resilient member is less than 57.5% of a total area of the resilient layer bounding box.

10. The nasal dilator of claim 9 wherein the first resilient member and the second resilient member are interconnected by a portion of the base layer or the cover layer, at least at lateral ends of the first and second resilient members.

11. The nasal dilator of claim 9 wherein the resilient member gap is pierced by at least one opening.

12. The nasal dilator of claim 9 wherein the resilient layer consists of the first resilient member and the second resilient member.

13. The nasal dilator of claim 12 wherein the first resilient member and the second resilient member extend fully from end to end of the nasal dilator.

14. The nasal dilator of claim 9, wherein the first resilient member and second resilient member are integrated into the at least one of the base layer and the cover layer by being constrained at both lateral ends thereof, respectively, by the at least one of the base layer and the cover layer.

\* \* \* \* \*